(12) United States Patent
Kokubo et al.

(10) Patent No.: US 7,829,196 B2
(45) Date of Patent: *Nov. 9, 2010

(54) HARD TISSUE REPAIRING MATERIAL

(75) Inventors: Tadashi Kokubo, 50, Umegaoka 2-chome, Nagaokakyo-shi, Kyoto (JP) 617-0841; Masahiro Nawa, Osaka (JP); Masaki Uchida, Bozeman, MT (US)

(73) Assignees: Panasonic Corporation Works, Ltd., Kadoma-shi (JP); Tadashi Kokubo, Nagaokakyo-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/420,244

(22) Filed: Apr. 8, 2009

(65) Prior Publication Data

US 2009/0191280 A1 Jul. 30, 2009

Related U.S. Application Data

(63) Continuation of application No. 10/111,388, filed as application No. PCT/JP00/07642 on Oct. 31, 2000, now Pat. No. 7,611,781.

(30) Foreign Application Priority Data

Nov. 2, 1999 (JP) .................................. 11-312346
Jan. 18, 2000 (JP) ............................. 2000-009243

(51) Int. Cl.
*B32B 9/00* (2006.01)

(52) U.S. Cl. ........................ 428/469; 428/472; 428/699; 428/701; 428/702

(58) Field of Classification Search ....................... None
See application file for complete search history.

(56) References Cited

U.S. PATENT DOCUMENTS 3,254,949 A * 6/1966 Clearfield .................... 423/608

OTHER PUBLICATIONS

M. Uchida, et al., "Apatite-Forming Ability of Zirconia Gel in Modified SBF", Bioceramics, vol. 11, pp. 77-80, XP-000989634, (1998).

* cited by examiner

*Primary Examiner*—Timothy M Speer
(74) *Attorney, Agent, or Firm*—Oblon, Spivak, McClelland, Maier & Neustadt, L.L.P.

(57) ABSTRACT

A hard tissue repairing material includes zirconia as a base material. A surface of the base material has a hydrophilic group. The hydrophilic group is bonded to zirconium atom in the base material. The base material may contain at least an ionic component that is selected from a group consisting of calcium ion, sodium ion, potassium ion, and phosphate ions within the surface. A hard tissue repairing material may include zirconia as a base material and a layer of a main component of an apatite. The layer of the apatite may be formed on a hydrophilic group bonded to zirconium atom in the base material.

10 Claims, No Drawings

HARD TISSUE REPAIRING MATERIAL

This application is a Continuation of U.S. application Ser. No. 10/111,388, filed on Aug. 16, 2002, which is a National Stage of PCT/JP00/07642 filed on Oct. 31, 2000.

TECHNICAL FIELD

The present invention relates to a hard tissue repairing materials and, particularly, to a bone repairing that is used to repair when articular function and/or bone function of hands and feet are lost. Furthermore, the invention relates to an implant, that can be used as an artificial tooth root, for rebuilding the teeth and tusks when the teeth had been lost because of senility or illness.

BACKGROUND ART

Generally, metallic materials, for example, stainless steel and titanium metal and titanium alloys, ceramic materials, for example, hydroxyapatite (HAP), bioactive-glass, alumina, and zirconia have been used as biomaterials in practical use. The metallic materials have a good strength and good toughness (tolerance of catastrophic fracture), but have poor corrosion resistance for use in living body. There is a danger of damaging the living tissue because of an elution of metallic materials in living body. The hydroxyapatite and the bioactive-glass have a property of bonding to a living bone (that is to say bioactivity), so that the hydroxyapatite and the bioactive-glass are turned to practical use as bone compensatory materials, a periodontal filling materials, an artificial vertebra body, and any spacer. These materials have a strength and a toughness that is much less than that of a living bone, so that these materials have not been used as portions that is under high load-bearing conditions, e.g. a femoral bone and tibial bone, and an artificial root of a tooth. As compared with a hydroxyapatite and bioactive-glass, alumina has a high strength and a high toughness. However, application of the alumina and the zirconia as a bone repairing material is limited because of non-bioactivity. Alumina had been turned to a practical use as an artificial root of a tooth, but now the alumina was replaced by titanium metal and titanium alloys because of fragile property peculiar to the ceramics.

As described above, the metallic materials, e.g. titanium metal and titanium alloys, and the ceramics materials, e.g. alumina and zirconia are non-bioactive materials that cannot bond to the living bone. Preferably, the bioactive layer that has a good adhesive property to bone are formed, and the bioactive function are given on the surface of the non-bioactive materials, in order that the materials are used as a bone repairing material and an artificial root of a tooth. Several prior art methods of forming the bioactive layer on the materials have been disclosed. For example, a method of forming a layer on base materials by a sputtering process or evaporation process is disclosed. The Japanese Laid-open Patent Publication No. 4-242659 discloses a method of forming a layer on base materials by plasma spraying. The Japanese Laid-open Patent Publication No. 1-203285 discloses a method of forming the mixture of zirconia and apatite on the surface of a zirconia cast by coating and sintering, with the base material limited to zirconia in view of the high strength and high toughness.

By the way, several prior art methods of giving the bioactive function at the surface of a base materials are disclosed. The Japanese Laid-open Patent Publication No. 6-23030 discloses a method of forming a coating layer of silica gel or titania gel on the surface of a base material. The Japanese Laid-open Patent Publication No. 10-179718 discloses a method of improving the surface of a base material of titanium metal and titanium alloys to bioactive by soaking in an alkaline fluid.

To form the bioactive layer on the surface of the base materials, the layer by sputtering, evaporation, and plasma spraying cannot have good contact strength to the base materials. Regarding with the layer formed by the Japanese Laid-open Patent Publication No. 1-203285, the bioactivity is declined because of increasing the ratio of zirconia in the mixture of the zirconia and the apatite, while the adhesive strength is declined because of increasing the ratio of apatite in the mixture. The layer having the hydroxyl group formed by the method of the Japanese Laid-open Patent Publication No. 6-23030 are the silica gel layer or the titania gel layer on the surface of the base materials. Similarly, the bioactive layer formed by the method of the Japanese Laid-open Patent Publication No. 10-179718 are titania phase, titania gel phase, alkaline-titanate phase, and alkaline-titanate gel phase.

DISCLOSURE OF INVENTION

Therefore, it is an object of the present invention to provide a hard tissue repairing material with high mechanically property and high bioactivity.

In accordance with one aspect of the present invention, there is provided a hard tissue repairing material including zirconia as a base material. A surface of the base material has a hydrophilic group, which is bonded to zirconium atom in the base material.

The base material including the zirconia means that including at least zirconium dioxide ($ZrO_2$). The base material may be combined with other materials, e.g. alumina. The base material may include a stabilizing agent. The hydrophilic group on the surface of the base material may be a hydroxyl group, a carboxyl group, amino group, carbonate group, sulfonic acid group, and phosphoric group. Specifically, the hydroxyl group is preferable as functional group capable of inducing the nucleus creation of hydroxyapatite ($Ca_{10}(PO_4)_6(OH)_2$).

According to the hard tissue repairing material of this invention, it has a good strength and a good toughness because of the inclusion of the zirconia with good mechanically property. According to the hydrophilic group on the surface, an apatite layer may be formed on the surface of the base material in the living body, or in the simulated body fluid (hereunder called as "SBF") with ion concentrations nearly equal to those of human body fluid. The apatite (hereunder called as "bone-like apatite") is the hydroxyapatite which has carbonate ion ($CO_3^{2-}$) and low Ca ion concentration (Ca deficiting) regarding with stoichiometric composition ($Ca_{10}(PO_4)_6(OH)_2$). The bone-like apatite also has a Ca/P ratio that is lower than 1.67 of the stoichiometric hydroxyapatite. The bone-like apatite has a plurality of lattice defect and is constructed by fine particles. Therefore, the bone-like apatite is nearly equal to the bone apatite of living bone. The bone-like apatite is formed on the surface of the base material, so that an osteoblast actively grows, differentiates, and forms a collagen and a bone apatite on the bone-like apatite. That is to say, a new bone tissue is grown from the surrounding living bone to the surface of the bone-like apatite layer. Then a chemical bond between the bone apatite of living bone and the bone-like apatite is formed, so that the base material may be strongly bonded to the living bone.

Therefore, in order that the artificial materials can bond to the living body, it is necessary that the bone-like apatite may be formed on the surface of the artificial materials in the living body. The hard tissue repairing material of this invention has the hydrophilic group, which is bonded to a zirconia in the base material, on the surface without any gel phase so that the hydrophilic group induced a bone-like apatite nucleation on the surface of the base material. Then, the bone-like apatite is bonded to both the base material and the living bone, so high adhesive strength between the base material and the living bone may be given.

The zirconia in the base material is preferably a tetragonal zirconia polycrystals with high strength and high toughness. Preferably, the base material includes a stabilizing agent, e.g. ceria and yttria used as stabilizing tetragonal phase. In the presence of the stabilizing agent, the tetragonal zirconia polycrystals can have a high strength and a high toughness. Specifically, a tetragonal zirconia polycrystals stabilized with ceria (Ce-TZP) has a good phase stability without a tetragonal-to-monoclinic phase transition, so that the Ce-TZP can keep stably tetragonal phase without a degradation of property in the living body and at the hard atmosphere e.g., moisture atmosphere with vapor. Therefore, the base material contains preferably at least an ceria as a stabilizing agent. As compared with the tetragonal zirconia polycrystals stabilized with yttria (Y-TZP), the Ce-TZP has a very high toughness, but has a less strength and a less hardness than those of the Y-TZP. Therefore, in order to compensate for the modest properties, the base materials containing zirconia is preferably taken into composite materials with an alumina having high hardness as secondary phase. In many composite materials, a zirconia/alumina nano-composite with ceria, which may have nanometer sized alumina particles partly trapped within a zirconia crystal particle, indicates much more excellent mechanical properties than those of the Y-TZP (see Japanese Patent No. 2703207). Therefore the zirconia/alumina nano-composite is preferably used as the base material of this invention. Alternatively, the base material may contain both ceria and yttria as the stabilizing agent.

The zirconia contained in the base material may not be only the tetragonal zirconia polycrystals but also partially stabilized zirconia (PSZ), which has a magnesia or a calcia as a stabilizing agent. The tetragonal zirconia polycrystals and the partially stabilized zirconia may contain a small quantity of impurities, such as hafunia and titania.

The hydrophilic group on the surface of the base material is preferably a hydroxyl group (OH group). The Zr—OH group is a functional group that may induce an apatite nucleation, so that the bone-like apatite layer may be formed on the surface of the base materials in the living body, or in the SBF. The human body fluid has calcium ions ($Ca^{2+}$) and phosphate ions ($PO_4^{3-}$) highly supersaturated with respect to apatite. Therefore, in the living body, the Zr—OH group on the surface takes the calcium ions, then the Zr—OH group takes the phosphate ions and the carbonate ions, so a lot of spherical apatite nuclei is formed on the base materials. The apatite nuclei grows while taking the above ions, so the bone-like apatite may be formed on the base materials spontaneously. Thus, with the hydroxyl group introduced as the hydrophilic group on the surface of the base materials containing zirconia, the base materials with non-bioactivity may be given a bioactivity that is capable to bond to a living bone with chemical bond. This hydroxyl group is bonded to a zirconium atom of the zirconia in the base material. The hydroxyl group may be formed by modifying the surface of zirconia in the base material.

The base material may contain at least one ionic component selected from a group consisting of calcium ion, sodium ion, potassium ion, and phosphate ions within the surface. With the ionic component contained within the surface of the base material, the ionic components of calcium ion, sodium ion, potassium ion, and phosphate ions etc are eluted from the surface of the base materials in a human body fluid of a living body, and in the simulated body fluid. In the meantime, the eluted ionic components in the human body fluid increase the ion concentrations, such as the hydroxyl ions and calcium ions, etc. Consequently, ionic activity product of apatite rises, and may hasten the bone-like apatite layer formation on the base materials in a human body fluid of a living body, or in the simulated body fluid. If the bone-like apatite layer is formed on the surface of the base material soaked in SBF, a bonding period with the base material and a living bone in a living body may be shortened. It is noted that the thickness of this layer is preferably 1-50 micrometer.

A process for producing a hard tissue repairing material includes preparing a base material that has at least a zirconia exposed to the surface of the base material, and forming a hydrophilic group on the surface of the base material.

The step of forming the hydrophilic group on the surface of the base material may be soaking the base material in an alkaline aqueous solution or an acid aqueous solution.

The alkaline solution is alkaline, for example, a solution containing a sodium hydroxide, a potassium hydroxide, etc. The acid aqueous solution is acid, for example, a solution containing a hydrochloric acid, a nitric acid, a sulfuric acid, and phosphoric acid. Regarding with a condition of soaking the base material in the alkaline aqueous solution or the acid aqueous solution, a concentration of the alkaline aqueous solution or the acid aqueous solution is preferably 0.5-20 mol/l, a condition of temperature is preferable 60-140° C.

It is considered that an $OH^-$ ion in alkaline solution or a $H_3O^+$ ion in acid solution may cut a bond of Zr—O of zirconia in the base material, according to soaking the base material with zirconia on the surface in the alkaline aqueous solution or the acid aqueous solution. Then a Zr—OH group, which is bonded to a zirconium atom, may be formed on the surface of the base material. The Zr—OH has a bioactive property. It is a new discovery that zirconia, which is not classified as the amphoteric oxide, may be improved by both an alkaline aqueous solution and an acid aqueous solution. Furthermore, it is also a new discovery that the hydroxyl group on the surface, which is bonded to a zirconium atom of the zirconia in the base material, can induce a nucleus creation of hydroxyapatite. However, a hydrophilic group formed on an alumina gel that is classified as amphoteric oxide cannot induce an apatite nucleation by soaking in SBF (Journal of Biomedical Materials Research, 1994, Vol. 28, pp 7-15).

It is known that an OH group on a zirconia gel made by the sol-gel process may induce a nucleus creation of apatite (Biomeramics volume 11 Ed. by R. Z. LeGros and J. P. LeGros, World Scientific, (1998) pp 77-80). This zirconia gel is amorphous phase. Even though same Zr—OH group, compared the Zr—OH group on the surface of tetragonal zirconia and monoclinic zirconia of this invention with the Zr—OH on the zirconia gel of amorphous phase, Zr—OH of this invention has high inducement to a nucleus creation of apatite. It is considered that the apatite may be easily grown on rather Zr—OH formed on the surface with crystal structure than Zr—OH formed on the surface with no crystal structure, because the OH group of the apatite have a coordination to a crystal direction of the Zr—OH of this invention, when the apatite is created.

In further aspect of the present invention, the process for producing a hard tissue repairing material further includes incorporating an ionic component within the surface of the base material after soaking the base material in an alkaline aqueous solution or an acid aqueous solution.

The incorporating the ionic component within the surface of the base material is preferably soaking the base material in a molten salt containing at least an ionic component selected from the group consisting of calcium ion, sodium ion, potassium ion, and phosphate ions.

In this process, the hydrophilic group is initially formed on the base material, the ionic component is secondly incorporated within the base material. Any combination of salts selected from the group consisting of nitrate, acetate, for example calcium nitrate, sodium nitrate, and potassium nitrate, and other carbonate, chloride, and phosphate may be used as the molten salt. Preferably, the eutectic mixture in eutectic point, at which the melting point is lowest, is used for each salt combination.

The incorporating the ionic component within the surface of the base material is preferably soaking the base material in an aqueous solution containing at least an ionic component selected from the group consisting of calcium ion, sodium ion, potassium ion, and phosphate ions.

In this process, the ionic component is initially incorporated within the base material, secondly, the hydrophilic group is formed on the base material. The aqueous solution is a solution containing a metallic hydroxide, for example, calcium hydroxide and potassium hydroxide, and a solution of calcium chloride dissolving in dilute hydrochloric acid, and a solution of sodium nitride or potassium nitride dissolving in dilute nitric acid. The concentration of the solution is preferably 0.5-20 mol/l, and the temperature of the solution is preferably 60-140° C.

In a yet further aspect of the present invention, the process for producing a hard tissue repairing material further includes incorporating an ionic component within the surface of the base material and before forming the hydrophilic group on the surface of the base material.

The incorporating the ionic component within the surface of the base material is preferably soaking the base material in a molten salt containing at least an ionic component selected from the group consisting of calcium ion, sodium ion, potassium ion, and phosphate ions.

The incorporating the ionic component within the surface of the base material is preferably soaking the base material in an aqueous solution containing at least an ionic component selected from the group consisting of calcium ion, sodium ion, potassium ion, and phosphate ions.

In a yet further aspect of the present invention, the process for producing a hard tissue repairing material further includes soaking the base material in the simulated body fluid with ion concentrations nearly equal to those of human body fluid.

It is noted that the base material is preferably at least a base material with zirconia exposed on the surface, before the base material soaked in the simulated body fluid. The base material has preferably a hydrophilic group on the surface. Moreover, the hydrophilic group is preferably bonded to a zirconium atom of zirconia in the base material. In this process, the bone-like apatite layer may be easily formed on the surface in the simulated body fluid, according to the hydrophilic group bonded to a zirconium atom of zirconia in the base material.

According to the hard tissue repairing material of this invention, it has a hydrophilic group, which is bonded to a zirconium atom of zirconia in the base material. Thus the hard tissue repairing material has a high hardness, a high toughness, and good bioactive property that indicates good bonding to a living bone. Therefore, the hard tissue repairing material can be used in bone repairing without a reinforcement e.g., metal or plastics. It can be used in the femoral bone and the tibial bone, which is received with a large load. The hard tissue repairing material can supersede a prosthetic titanium metal screw widely used as an artificial root of a tooth, because the hard tissue has sufficient mechanically property and high bioactive property. In this case of the artificial root of a tooth, the usage may not be limited in screw type. The hard tissue repairing material may not injure the living tissue because of ceramics. Therefore, the hard tissue repairing material of zirconia ceramics of this invention is suitably used in a bone repairing material and a implant e.g., an artificial root of a tooth.

BEST MODE FOR CARRYING OUT THE INVENTION

A hard tissue repairing material includes a base material containing zirconia. The base material has a hydrophilic group on the surface. Moreover, the hydrophilic group is bonded to a zirconium atom of zirconia in the base material. The hydrophilic group has bioactive property, so may easily induce a nucleus creation of apatite on the surface of the base material in the living body or in the simulated body fluid. The tetragonal zirconia polycrystals is used because of high mechanical property. The base material may be composite incorporating with an alumina having good hardness. Therefore, the hard tissue repairing material provides a high mechanical property and a high bioactive property.

In the first embodiment, several discs (diameter 11 mm, thickness 1 mm) of zirconia-alumina composite are prepared as the base materials. The zirconia-alumina composite contains the tetragonal zirconia polycrystals with 10 mol % ceria as against the zirconia as a stabilizing agent and the alumina particles in 30 volume %. In the microstructure of this composite materials, a basic structure has a mixed morphology of micro and nano-composite materials, which have a submicron sized zirconia particles and alumina particles. Moreover, a part of the nanometer sized alumina particles are trapped within the zirconia crystal particles consisting of matrix phase. The process of forming the hydrophilic group on the surface of the base material is as following.

Several base materials are respectively soaked in 5 ml of concentrated hydrochloric acid, concentrated phosphoric acid, 50 volume % phosphoric acid, concentrated sulfuric acid, 50 volume % sulfuric acid, and 15 mol/l sodium hydroxide solution holding at 95° C. for 4 days. Then the base material are washed by distilled water, and dried up. This soaking process, in which the base materials are soaked in the acid solution or the alkaline solution, is called the "chemical process" hereunder.

The base materials performed of the chemical process and the base materials before the chemical process are soaked in the simulated body fluid (called "SBF" hereunder) (ion concentrations (mM): $Na^+$142, $K^+$5.0, $Mg^{2+}$1.5, $Ca^{2+}$2.5, $Cl^-$148, $HCO_3^-$4.2, $HPO_4^{2-}$1.0, $SO_4^{2-}$0.5) with 30 ml holding at pH 7.4, and 36.5° C. for several time. The surface of the base materials are analyzed by a thin film X-ray diffraction method (TF-XRD), X-ray photo-electron spectroscopy (XPS), before the chemical process, after the chemical process, and after soaking in SBF. Moreover, the surfaces are observed by scanning electron microscope (SEM). The element analysis is observed by Inductively coupled plasma atomic emission spectrometry (ICPA). For the component contents analysis, the qualitative analysis is observed by Fourier transform infrared spectroscopy (FT-IR), and the quantitative analysis is observed by thermal analysis. In the thermal analysis, a $CO_2$ gas and a $H_2O$ gas are detected in a burning gas, so a carbonate ion ($CO_3^{2-}$) content with respect to the deposits is observed.

As a result of this analysis and observation, in TF-XRD patterns and SEM images, the base materials preformed by the chemical process and not preformed before soaking in the SBF have no difference. However, new spherical deposits are observed by SEM in the surface of the base materials soaked in SBF for 14 days after the chemical process regardless of any solution of the chemical process. According to a peak of TF-XRD patterns of the base materials soaked in SBF belonging to an apatite, the deposits are identified to the apatite. The apatite, which has been soaked in 50 volume % phosphoric acid, has a Ca/P ration that is 1.51 observed by ICPA, and has a carbonate ion content that is 2.64 wt % with respect to the apatite observed by thermal analysis. Therefore, the apatite may be bone-like apatite. The amounts of the deposits per area differ depending on the kind of solution of the chemical process. Thus the amounts of apatite are arranged in the following order; 50 volume % phosphoric acid>50 volume % sulfuric acid>15 mol/l sodium hydroxide solution>concentrated hydrochloric acid>concentrated sulfuric acid>concentrated phosphoric acid. It is noted that the apatite didn't have been deposited on the surface of the base materials not performed by the chemical process.

The spectrum of 1 s orbital electron of oxide in XPS data is separated into Zr—OH, Al—OH, and adsorbed water (first group), $ZrO_2$, and $Al_2O_3$ (second group). Then, in the case of the base materials performed in the chemical process, the spectrum strength of the Zr—OH group and the Al—OH group increase regardless of a kind of solution of the chemical process. Therefore, according to the chemical process, Zr—OH group and Al—OH group may be formed on the surface of the base materials. It is considered that the Zr—OH group induces the apatite nucleation, because the Al—OH cannot induce the apatite nucleation.

In the second embodiment, the base materials performed in the chemical process in similar conditions of the first embodiment are prepared. The base materials performed in the chemical process are soaked in the molten salt, so that a calcium ion and a potassium ion are contained within the surface of the base materials. The steps of soaking in the molten salt are performed as following. A calcium carbonate and a potassium carbonate is mixed in a mixing ratio of 6:4, and this mixture is melted at 850° C., then a carbonate molten salt is given. The base materials, which have been preheated at 750° C., are soaked for one hour. Then the base materials are washed by distilled water, and dried. Hereunder, this process of soaking in the molten salt is called as the "molten salt process". According to XPS analysis for the surface of the base materials, peaks of a calcium and potassium is detected. Therefore, it is ascertained that the base materials have the calcium ion and the potassium ion within the surface.

The base materials, which are performed in the chemical process and the molten salt process in this order, are soaked in the SBF with pH 7.4 and 36.5° C. for 7 days. Many spherical bone-like apatite crystals form on the surface of the base materials as observed by SEM.

In the third embodiment, the base materials performed in the chemical process in similar conditions of the first embodiment are prepared. The base materials performed in the chemical process are soaked in the molten salt that is different from the second embodiment, so that a calcium ion and a sodium ion are contained within the surface of the base materials. The steps of soaking in the molten salt are performed as following. A calcium nitrate and a sodium nitrate is mixed in a mixing ratio of 5:5, and this mixture is melted at 300° C., then a nitrate molten salt is given. The base materials, which have been preheated at 200° C., are soaked for one hour. Then the base materials are washed by distilled water, and dried.

According to XPS analysis for the surface of the base materials, peaks of a calcium and sodium are detected. Therefore, it is ascertained that the base materials have the calcium ion and the sodium ion within the surface.

The base materials, which are performed in the chemical process and the molten salt process in this order, are soaked in the SBF with pH 7.4 and 36.5° C. for 7 days. Many spherical bone-like apatite crystals form on the surface of the base materials as observed by SEM.

In the fourth embodiment, the base materials performed in the chemical process in similar conditions of the first embodiment are prepared. The base materials performed in the chemical process are soaked in the molten salt that is different from the second and third embodiment, so that a calcium ion and a sodium ion are contained within the surface of the base materials. The steps of soaking in the molten salt are performed as following. A calcium chloride and a sodium chloride is mixed in a mixing ratio of 5:5, and this mixture is melted at 580° C., then a chloride molten salt is given. The base materials, which have been preheated at 480° C., are soaked for one hour. Then the base materials are washed by distilled water, and dried. According to XPS analysis for the surface of the base materials, peaks of a calcium and sodium is detected. Therefore, it is ascertained that the base materials have the calcium ion and the sodium ion within the surface.

The base materials, which are performed in the chemical process and the molten salt process in this order, are soaked in the SBF with pH 7.4 and 36.5° C. for 7 days. Many spherical bone-like apatite crystals form on the surface of the base materials as observed by SEM.

In the fifth embodiment, the base materials (disc with diameter 11 mm, thickness 1 mm) of zirconia-alumina composite are prepared. The base materials are soaked in the molten salt, so that a calcium ion and a potassium ion are contained within the surface of the base materials. The steps of soaking in the molten salt are performed as following. A calcium carbonate and a potassium carbonate is mixed in a mixing ratio of 6:4, and this mixture is melted at 850° C., then a carbonate molten salt is given. The base materials, which have been preheated at 750° C., are soaked for one hour. Then the base materials are washed by distilled water, and dried. According to XPS analysis for the surface of the base materials, peaks of a calcium and potassium is detected. Therefore, it is ascertained that the base materials have the calcium ion and the potassium ion within the surface.

Several base materials are respectively soaked in 5 ml of 50 volume % phosphoric acid, and 15 mol/l sodium hydroxide solution holding at 95° C. for 4 days. Then the base material are washed by distilled water, and dried up.

The base materials, which are performed in the molten salt process and the chemical process in this order, are soaked in the SBF with pH 7.4 and 36.5° C. for 7 days. Many spherical bone-like apatite crystals form on the surface of the base materials as observed by SEM. The bone-like apatite has a Ca/P ratio that is within 1.48 to 1.56, and has a carbonate ion content that is within 2.5 to 3.5 wt % with respect to the bone-like apatite. It is noted that the bone-like apatites are similarly observed on the base materials, which is performed in the molten salt process of the third and the fourth embodiment and the chemical process in this order.

The invention claimed is:

1. A hard tissue repairing material, comprising:
   a base material made of zirconia including a plurality of zirconium atoms; and
   hydrophilic groups each bonded to one of the zirconium atoms constituting the surface of the base material, wherein the hydrophilic groups exist on the surface of the base material,
   wherein said zirconia in the base material is a tetragonal zirconia polycrystal.

2. A hard tissue repairing material according to claim 1, wherein said hydrophilic groups are hydroxyl groups.

3. A hard tissue repairing material, comprising:
   a base material made of zirconia including a plurality of zirconium atoms; and
   hydrophilic groups each bonded to one of the zirconium atoms constituting the surface of the base material, wherein the hydrophilic groups exist on the surface of the base material,
   wherein said base material includes at least a ceria as a stabilizing agent.

4. A hard tissue repairing material according to claim 3, wherein said hydrophilic groups are hydroxyl groups.

5. A hard tissue repairing material, comprising:
   a base material made of zirconia including a plurality of zirconium atoms; and
   hydrophilic groups each bonded to one of the zirconium atoms constituting the surface of the base material, wherein the hydrophilic groups exist on the surface of the base material,
   wherein said base material contains at least one ionic component that is selected from the group consisting of calcium ion, sodium ion, potassium ion, and phosphate ions within said surface.

6. A hard tissue repairing material according to claim 5, wherein said hydrophilic groups are hydroxyl groups.

7. A hard tissue repairing material according to claim 5, wherein said base material contains calcium ion.

8. A hard tissue repairing material according to claim 5, wherein said base material contains sodium ion.

9. A hard tissue repairing material according to claim 5, wherein said base material contains potassium ion.

10. A hard tissue repairing material according to claim 5, wherein said base material contains phosphate ions.

* * * * *

UNITED STATES PATENT AND TRADEMARK OFFICE
CERTIFICATE OF CORRECTION

PATENT NO. : 7,829,196 B2
APPLICATION NO. : 12/420244
DATED : November 9, 2010
INVENTOR(S) : Tadashi Kokubo et al.

It is certified that error appears in the above-identified patent and that said Letters Patent is hereby corrected as shown below:

On the title page, Item (73), the first Assignee's name is incorrect. Item (73) should read:

-- (73) Assignees: Panasonic Electric Works, Ltd., Kadoma-shi (JP);
Tadashi Kokubo, Nagaokakyo-shi (JP) --

Signed and Sealed this
Seventeenth Day of May, 2011

David J. Kappos
*Director of the United States Patent and Trademark Office*

UNITED STATES PATENT AND TRADEMARK OFFICE
CERTIFICATE OF CORRECTION

PATENT NO. : 7,829,196 B2
APPLICATION NO. : 12/420244
DATED : November 9, 2010
INVENTOR(S) : Tadashi Kokubo et al.

Page 1 of 1

It is certified that error appears in the above-identified patent and that said Letters Patent is hereby corrected as shown below:

Title page, Item (56), add the following:

--U.S. PATENT DOCUMENTS

| | | |
|---|---|---|
| 5,728,636 | 03/1998 | NAWA ET AL |
| 5,910,462 | 06/1999 | GANI ET AL |
| 6,022,400 | 02/2000 | IZUMI ET AL |
| 6,194,481 | 02/2001 | FURMAN ET AL |
| 5,356,436 | 10/1994 | NONAMI ET AL |
| 6,569,547 | 05/2003 | NAWA ET AL |
| 4,983,182 | 01/1991 | KIJIMA ET AL |
| 5,192,325 | 03/1993 | KIJIMA ET AL |
| 5,007,932 | 04/1991 | BEKKI ET AL |
| 5,185,177 | 02/1993 | KIJIMA ET AL |
| 3,860,529 | 01/1975 | HAMLING |
| 4,520,114 | 05/1985 | DAVID |

FOREIGN PATENT DOCUMENTS

| | | |
|---|---|---|
| EP | 0 389 713 | 10/1990 |
| JP | 06-023030 | 02/1994 |
| JP | 04-242659 | 08/1992 |
| JP | 01-203285 | 08/1989 |
| JP | 10-179718 | 07/1998 |
| JP | 08-268755 | 10/1996 |
| JP | 07-206600 | 08/1995 |
| JP | 01-242067 | 09/1989 |
| WO | 95/04012 | 02/1995 |
| JP | 09-503989 | 04/1997 |

OTHER PUBLICATIONS
P. Li, et al., "The Role of Hydrated Silica, Titania, And Alumina In Inducing Apatite On Implants", Journal of Biomedical Materials Research, vol. 28, 1994, pp. 7-15.--

Signed and Sealed this
Twenty-fifth Day of September, 2012

David J. Kappos
*Director of the United States Patent and Trademark Office*